United States Patent [19]

Lorenzi et al.

[11] Patent Number: 4,633,620
[45] Date of Patent: Jan. 6, 1987

[54] SYSTEM FOR PROCESSING OF STEEL BILLETS OR THE LIKE TO REMOVE SURFACE DEFECTS

[75] Inventors: Donald E. Lorenzi; Helmut F. Wagerer, both of Des Plaines, Ill.

[73] Assignee: Magnaflux Corporation, Chicago, Ill.

[21] Appl. No.: 788,080

[22] Filed: Oct. 16, 1985

Related U.S. Application Data

[63] Continuation of Ser. No. 531,165, Sep. 9, 1983, abandoned, which is a continuation-in-part of Ser. No. 407,656, Aug. 12, 1982, Pat. No. 4,502,253.

[51] Int. Cl.$^4$ .............................................. B24B 19/00
[52] U.S. Cl. ................................ 51/165 R; 51/165.72; 51/165.92; 51/35; 51/93; 266/51; 409/139; 409/149; 409/164
[58] Field of Search ........... 51/165 R, 165.71, 165.72, 51/165.73, 165.74, 165.75, 165.76, 165.92, 45, 92 R, 92 ND, 93, 326, 327, 281 R, 35; 144/2 M, 332, 330; 409/139, 149, 164; 266/51

[56] References Cited

U.S. PATENT DOCUMENTS

| | | | |
|---|---|---|---|
| 3,028,021 | 4/1962 | Peras | 266/51 X |
| 3,496,831 | 2/1970 | Eibe et al. | 51/92 R X |
| 3,953,943 | 5/1976 | Nakaoka | 51/165.92 X |
| 3,978,624 | 9/1976 | Merkel et al. | 51/165.92 |
| 3,992,826 | 11/1976 | Nakaoka | 51/165.72 X |
| 4,074,982 | 2/1978 | Koch et al. | 51/92 R |
| 4,112,626 | 9/1978 | Watanabe et al. | 51/165.72 X |
| 4,318,439 | 3/1982 | Hiroshima et al. | 266/51 X |
| 4,336,923 | 6/1982 | Shiraiwa et al. | 266/51 |

Primary Examiner—Robert P. Olszewski
Attorney, Agent, or Firm—Neuman, Williams, Anderson & Olson

[57] ABSTRACT

Methods and apparatus are disclosed for processing of steel billets or the like to remove surface defects. A material-removing device such as a grinding wheel is automatically controlled to initiate removal of material at points where defects have been detected and to continue removal of material as long as cracks or other defects continue to be detected. In certain disclosed embodiments, an inspection is performed using magnetic particle or other inspection equipment, the initial removal of material being controlled therefrom. Thereafter, material-removal is controlled from signals produced by a probe which is carried in the removal device or adjacent thereto. In other disclosed embodiments, a thin layer of material is removed to permit detection of defects by a probe, the material-removal being both initiated and continued under control of probe signals.

11 Claims, 20 Drawing Figures

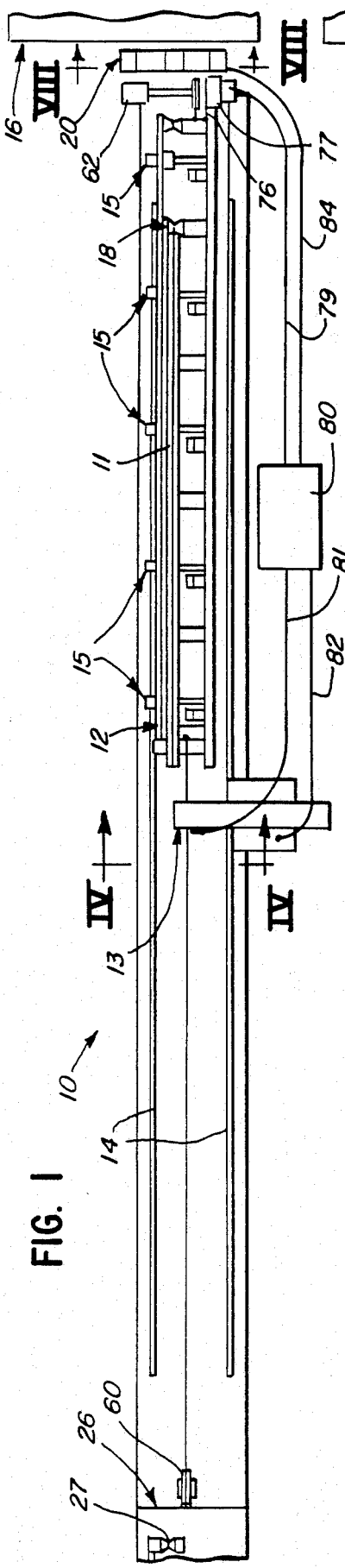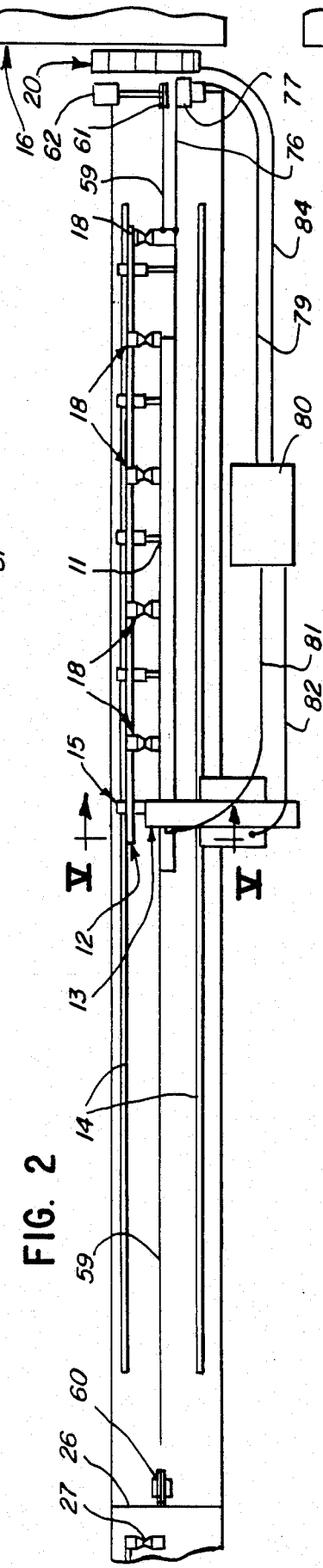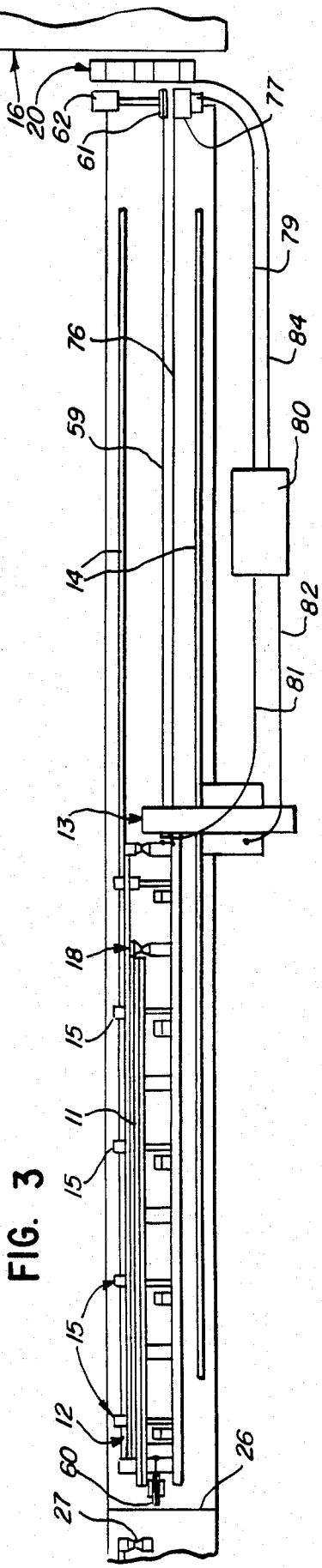

SYSTEM FOR PROCESSING OF STEEL BILLETS OR THE LIKE TO REMOVE SURFACE DEFECTS

This application is a continuation of our prior application Ser. No. 531,165, filed Sept. 9, 1983 now abandoned, which was a continuation-in-part of our application Ser. No. 407,656, filed Aug. 12, 1982, now U.S. Pat. No. 4,502,253, issued Mar. 5, 1985.

This invention relates to a system for removal of surface defects and more particularly to a system designed for removal of cracks in steel billets to obtain high quality end products. The system efficiently removes defective material, with minimum waste of material and it operates automatically with a high degree of reliability. The costs of construction and operation are low, making it possible to economically produce billets of very high quality.

BACKGROUND OF THE INVENTION

The control of quality of basic steel products such as bars, rods, plates, sheets and the like has become of increasing importance in recent years. One factor has been a greater demand for materials having high strength-to-weight ratios, for use in vehicles and other products. Another factor has been in the growing recognition of the waste which results when a purchaser of a basic steel product invests a substantial amount of time, materials and effort in manufacture of an end product and then finds it necessary to reject the end product after a final inspection because of a defect which existed in the basic steel product. Even more serious problems result when an end product contains a defect which is not found until later when the product is in use.

Certain very troublesome types of defects are encountered in connection with roller operations which are used in making a variety of steel products. After first casting steel as ingots, rolling operations are used to roll the ingots into slabs and to then roll the slabs into plates and sheets. Rolling operations are also used to roll ingots into blooms, to then roll the blooms into billets and to then roll billets into bars, rods and similar rolled products which may be used by manufacturers to make a great many different types of final products.

It is found that the slabs, blooms and billets initially rolled from ingots frequently contain longitudinal cracks in or near the surface thereof and that such cracks are not removed in subsequent rolling operations. On the contrary, each crack is usually increased in length in subsequent rolling operations and may cause a long length of the final rolled product to be defective.

In the prior art, various procedures have been used to detect cracks and to remove the surface portions of billets or other raw products which contain such cracks. To detect cracks, magnetic particle inspection has been used very successfully, magnetic particle inspection being very sensitive to cracks in or near the surface of a part. After detection of cracks, the portions which contain the cracks may be removed by using torches, by scarfing and milling procedures and by grinding procedures. Grinding procedures have been used increasingly in recent years and are highly effective so that the quality of the final rolled product can be substantially enhanced. However, a very high degree of skill and attention is required on the part of the grinding equipment operator, working in noisy and dirty conditions with poor visibility. It is very difficult to obtain a high degree of assurance that the billet or other raw product will be completely free of defective portions.

It is noteworthy that continuous casting procedures may be used in a manner such as to avoid certain problems connected with rolling procedures. However, the construction of plants for continuous casting involves huge capital expenditures and there exists a very large investment in rolling equipment which would be lost if an attempt were made to substitute continuous casting procedures for rolling procedures. Moreover, casting procedures are not without problems and rolling procedures have certain inherent advantages over casting procedures in the production of many types of products.

SUMMARY OF THE INVENTION

This invention was evolved with the general object of obtaining greatly improved quality of rolled steel products while permitting manufacture of such products economically, with minimal capital and operating expenses.

In accordance with the invention, a system is provided in which steel billets or similar primary products for use in rolling operations are inspected automatically to respond to defects therein and to remove automatically the portions of the parts containing such defects.

In one preferred system, a probe is positioned in proximity to the surface portion of a part which is engaged by a grinding wheel to detect defects in the part during a grinding operation. Signals developed by the probe are used for the automatic control of termination of the grinding operation so that only the defective portions of a part are moved. The probe may preferably be mounted in a grinding wheel in a manner as disclosed in our prior filed co-pending application, Ser. No. 407,656, filed Aug. 12, 1982. With such a mounting, a very high degree of sensitivity is obtained with respect to cracks or similar defects in the part and it is obtained during the grinding operation to immediately locate defects in the portion of the part being ground. In the alternative, the probe may be supported in a position adjacent the grinding wheel with means being provided for moving the probe into engagement with a portion of the part immediately after grinding thereof, to determine whether a defect still remains therein.

The invention is especially advantageous when applied to the grinding of surface defects from steel billets and preferred embodiments of the invention as described and illustrated herein are designed for such an application. It will be understood, however, that various features of the invention may be used for other applications.

In one embodiment of the invention, a steel billet is supported to allow removal of material therefrom by a grinding wheel with positioning means being provided to position the grinding wheel relative to the billet support. Preferably, the billet is movable longitudinally to position any selected portion thereof along its length in a position opposite the grinding wheel which is rotated on an axis parallel to the longitudinal axis of the billet. In addition, the billet may preferably be movable transversely relative to the grinding wheel, while the grinding wheel may be movable toward and away from the billet.

In accordance with an important feature of the invention, the relative movements of the grinding wheel and the billet are programmed in a manner such that substantial amounts of the material of the billet are removed only in regions which contain defects. In one embodiment of the invention, defective portions of the billet are located using a known type of testing apparatus such as magnetic particle inspection apparatus and detectable marks are applied to the surface of the billet where defects occur. Sensing means are provided for detecting such marks and for controlling the initiation of the grinding operation with respect thereto. After the grinding operation is initiated, the signals developed by the probe may be used for terminating the grinding operation, thereby limiting the amount of material removed from the billet.

In another embodiment of the invention, the locations of defective portions of a billet are recorded in a memory during a magnetic particle or other type of inspection performed prior to a grinding operation and at the same time, billet identification marks are applied. When any billet is subsequently moved into the grinding apparatus, such marks are detected to determine the identification of the billet and to recall the locations of defective portions from memory, for control of the grinding operation.

In still another embodiment of the invention, a grinding wheel is used to remove a very thin layer from the surface of the billet to permit sensitive and accurate detection of any cracks in the billet and the grinding operation is continued only with respect to defective portions of the billet.

Another feature of the invention relates to the provision of a handling and control arrangement such that the billet is turned 90 degrees on its axis to permit sequential processing of all four sides thereof.

Additional features of the invention relate to the processing of the billet in a manner such as to process each billet with a minimum amount of time while minimizing the possibility of any malfunction and obtaining a very high degree of reliability.

This invention contemplates other objects, features and advantages which will become more fully apparent from the following detailed description taken in conjunction with the accompanying drawings.

BRIEF DESCRIPTION OF THE DRAWINGS

FIG. 1 is a top plan view of a billet processing system constructed in accordance with the invention, a carriage of the system being shown in a billet-receiving position;

FIG. 2 is a top plan view similar to FIG. 1 but showing a billet shifted transversely to a clamped position, also showing the carriage moved longitudinally to an intermediate position;

FIG. 3 is a top plan view similar to FIGS. 1 and 2 but showing the carriage in a billet discharge position;

DESCRIPTION OF PREFERRED EMBODIMENTS

Figure 4:
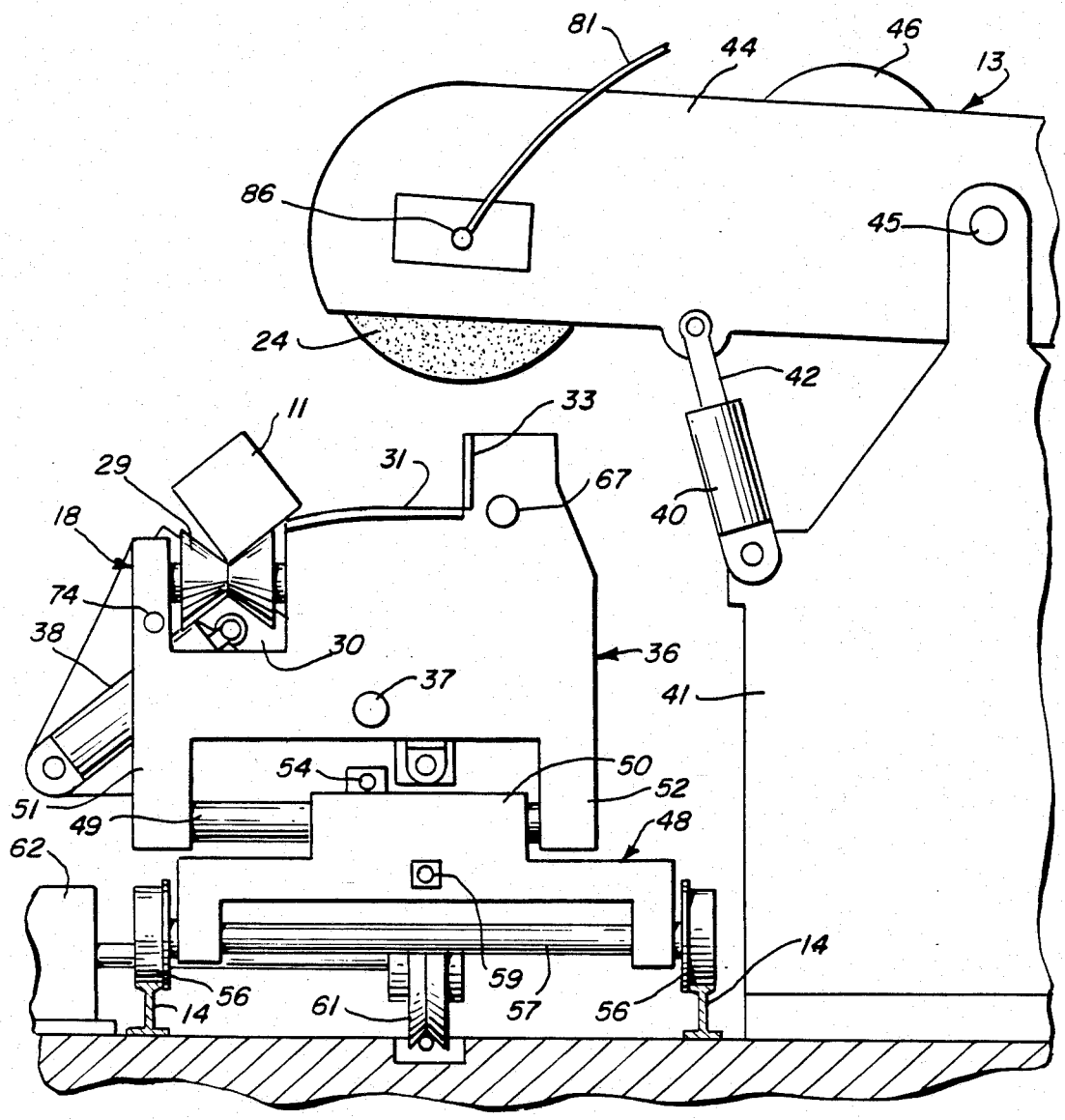
FIG. 4 is a sectional view taken substantially along line IV—IV of FIG. 1, providing a front elevational view of the carriage.

Reference numeral 10 generally designates a system constructed in accordance with the principles of the invention and particularly designed for processing of steel billets to remove longitudinal cracks in or near the surface thereof. It will be understood that various features of the invention have other applications.

In the system 10 as disagrammatically illustrated in the plan view of FIG. 1, a billet 11 is carried by a carriage 12 for processing by stationary grinding apparatus 13. The carriage 12 is supported on rails 14 for longitudinal movement and, during the processing operation, the billet is securely held on the carriage 12 by a series of longitudinally spaced assemblies 15 operative to support and clamp the billet 11 and also operative to index the billet 90 degrees on its axis, for sequential processing of all four faces thereof. FIG. 1 shows the carriage in an initial position with billet 11 being shown positioned on run-in, run-out rollers. FIG. 2 shows the billet 11 after being moved transversely and clamped in a grinding position and also shows the carriage 12 moved longitudinally to an intermediate position during the grinding operation.

Prior to processing by the grinding apparatus 13, the billet 11 may be inspected using inspection apparatus 16, an end portion of which is shown diagrammatically in FIG. 1. The inspection apparatus 16 may include magnetic particle inspection equipment and/or ultrasonic equipment and/or other equipment operative to detect surface or subsurface flaws. The location of any detected flaws may be indicated by applying pain or other marking material to the surface of the billet. A suitable apparatus is illustrated in the Gewartowski et al. U.S. Pat. No. 3,483,739 issued Dec. 16, 1969.

After inspection in the apparatus 16, the billet 11 may be moved longitudinally out of the apparatus 16, on run-out rollers thereof, and to a position as shown in FIG. 1, the billet being received and supported on run-in, run-out rollers of a series of longitudinally spaced roller assemblies 18 on the carriage 12. Then transfer and clamp arms of the assemblies 15 are operated to transversely shift and firmly clamp the billet, the billet being then positioned as shown in FIG. 2. Then the carriage 12 is moved longitudinally to the left to cause the upper surface of the billet to be moved under the grinding apparatus 13 which is automatically controlled to remove flaws or defects from the upper surface of the billet 11. After moving to the left and causing the entire length of one face to move under the grinding apparatus, the billet may be unclamped, rotated 90° and reclamped to be then moved longitudinally in the opposite direction.

Figure 5:
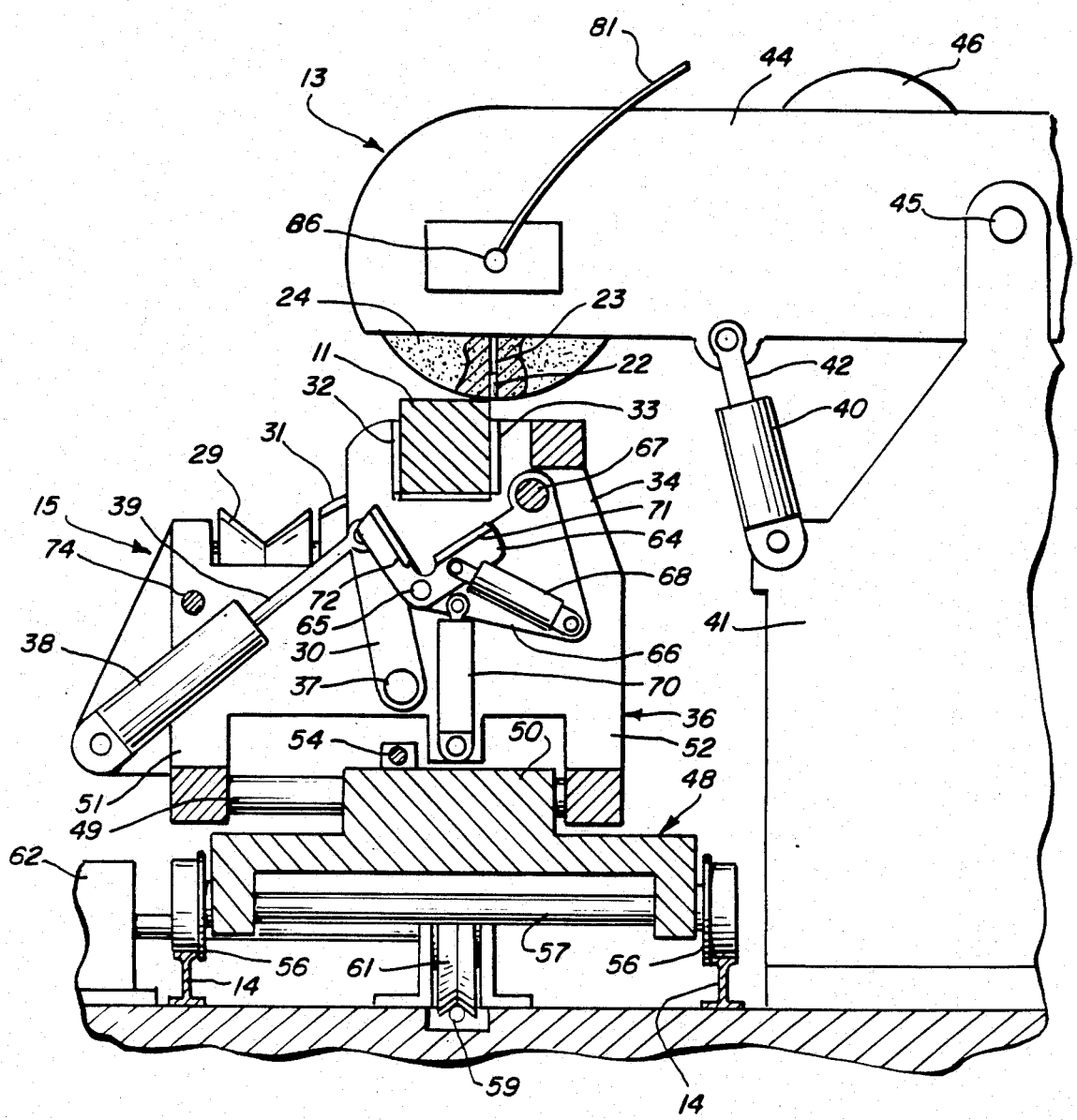
FIG. 5 is a sectional view taken substantially along line V—V of FIG. 2, showing a transfer and clamp arm assembly and a rotating arm assembly of the apparatus also showing the support of a crack detecting probe in a grinding wheel.

In the system 10 as illustrated, defect locating and signalling means are provided including a stationary optical sensing station 20 between the inspection equipment 16 and the receiving end of the carriage 12 when positioned as shown in FIG. 1. The station 20 is arranged for detection of marks previously applied to the surface of the billet during operation of the inspection equipment 16. The locating and signalling means also include a sensing probe associated with the grinding apparatus 13. As shown in FIG. 5, the sensing probe may be an eddy current probe 22 mounted in a radially extending passage 23 of a grinding wheel 24 of the grinding apparatus 13. The probe 22 operates to develop an electrical pulse as it passes over a crack in the surface of the billet 11.

The defect locating and signalling means of the system further includes signal storage means for storing signals developed by the optical sensing station, as hereinafter described.

The grinding apparatus 13 is operated in accordance with stored signals to move the grinding wheel 24 toward the billet 11 and to initiate removal of a portion containing a defect. During the removal operation, the output of the probe 22 is monitored and movement of the grinding wheel 24 toward the billet is continued as long as a defect signal is developed by the probe 22. However, when a signal is no longer developed by the probe 22, the wheel 24 is moved away from the billet, the billet is moved to position another defect-containing portion opposite the wheel 24 and another material-removal operation is effected. In this way, all portions of the billet which contain indicated defects are removed from the billet and very high quality is assured in subsequent rolling operations performed on the billet. At the same time, the unnecessary removal of defect-free material from the billet is minimized. Other important advantages are obtained, including the fact that billets may be rapidly processed and a high production rate can be attained.

After complete processing of all four sides of the billet, the carriage 12 may be in or moved to a position as shown in FIG. 3, and the assemblies 15 may be operated to move the billet 11 to the same position as shown in FIG. 1 in which it is supported on the run-in, run-out rollers of assemblies 18. The rollers of the assemblies 18 may then be operated as run-out rollers to transfer the billet 11 to a receiving section 26 including a receiving roller 27. Then the carriage 12 may be returned to the initial position as shown in FIG. 1 and another billet may be transferred thereto from the inspection apparatus 16.

FIG. 4 is an elevational sectional view which provides a front end view of the carriage 12 with the billet 11 positioned on the run-in, run-out rollers of the assemblies 18, such rollers being indicated by reference numeral 29. The billet 11 is illustrated as it is positioned prior to being transferred to and clamped in a grinding position. To transfer the billet to a grinding position, clamp arms 30 of the assemblies 15 are pivoted in a clockwise direction as viewed in FIG. 4, to lift the billet 11 off the rollers 29 and to slide the billet on transverse support surfaces 31 to a position as illustrated in FIG. 5 in which the billet 11 is clamped between face portions 32 of the clamp arms 30 and vertical face portions 33 of upright members 34 of a transversely movable frame structure 36 of the carriage 12.

The transfer and clamp arms 30 are mounted on a common horizontal longitudinally extending shaft 37 and are operated by hydraulic cylinders 38 which are pivotally mounted on the upright frame members 34 and which have piston rods 39 pivotally connected to the arms 30.

After the billet-transfer operation, the grinding wheel 24 is lowered to engage the upper face of the billet 11, as shown in FIG. 5. Vertical movement of the grinding wheel 24 is controlled by the hydraulic cylinder 40 which is pivotally connected to a stationary upright support structure 41 and which has a piston rod 42 connected to carrier structure 44 which journals the grinding wheel 24. The carrier structure 44 is pivotally supported by the shaft 45 from the upright stationary support structure 41. The grinding wheel is driven through a belt from an electric motor 46 mounted on the carrier structure 44.

In the illustrated grinding mechanism, both the grinding wheel 24 and the motor 46 are on the same side of the axis of the support shaft 45 and a counterbalance weight, not shown, is carried by the carrier structure 44 on the opposite side of the axis of the shaft 45.

The frame structure 36 is supported for transverse movement on a base frame 48 of the carriage 12. A series of longitudinally spaced horizontal cylindrical guide rods 49 are journalled in an upstanding portion 50 of the base frame 48 and are secured between depending portions 51 and 52 of the transversely movable frame structure 36. Transverse movement may be controlled by a series of horizontal lead screw assemblies, not shown, driven from a common longitudinally extending shaft 54 which is driven by an electric motor. The base frame structure is supported from the rails 14 by two pairs of flanged wheels 56 rigidly secured to opposite ends of shafts 57 which are journalled by the base frame structure 48.

To control longitudinal movement of the carriage 12, a cable 59 extends from a forward end of the base frame structure 48 to the upper side of a pulley 60 which is mounted adjacent the billet receiving section 26 as shown in FIG. 1. The cable 59 extends around the pulley 60 and from the lower side of the pulley 60 to a pulley or drum 61 which is mounted adjacent the inspection apparatus 16 to the rear of the carriage 12. The cable 59 extends from the upper side of the pulley 61 to a connection to the rearward end of the base frame structure 48 of the carriage 12. The pulley or drum 61 is driven by an electric motor 62 to effect longitudinal movement of the carriage 12.

To permit inspection of all four sides of a rectangular billet, a turning mechanism is provided which includes a generally L-shaped member 64 in each of the mechanisms 15, each member 64 being pivotally mounted on a shaft 65 which is carried by a plate 66. The plates 66 of all of the turning assemblies are mounted on a common shaft 67. The L-shaped members 64 are pivotal relative to the members 66 under control of hydraulic cylinders 68 and the plate members 66 are pivotal about the axis of the shaft 67 under control of hydraulic cylinders 70.

Figure 6:
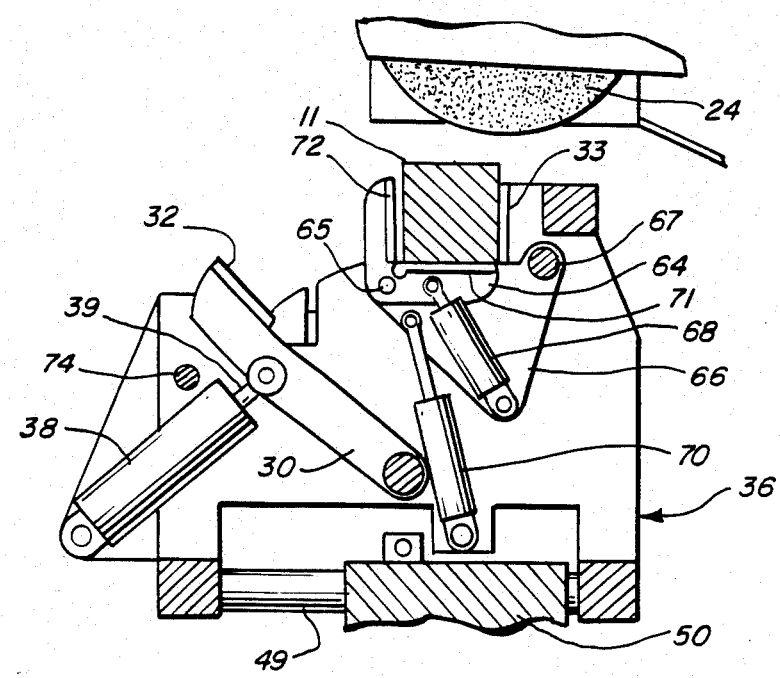
FIGS. 6 and 7 are sectional views similar to FIG. 5 but showing a turning mechanism in different positions, for depicting the operation thereof.
Figure 7:
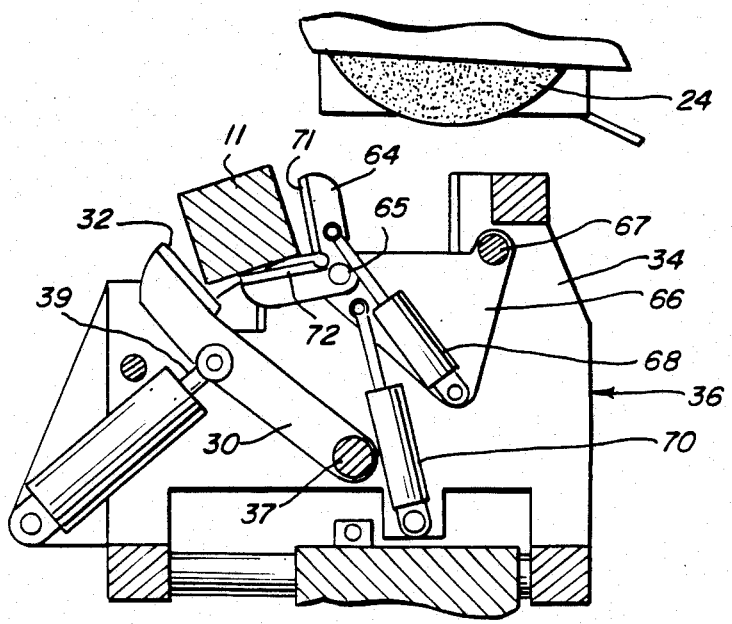

To turn the billet 11, the hydraulic cylinders 70 are operated to move the members 66 to positions as illustrated in FIG. 6 in which a face portion 71 of each L-shaped member 64 is in engagement with the lower side of the billet 11 and in which another engagement portion 72 of each member 64 is opposite one side of the billet 11. Then the cylinder 68 is operated to turn the billet 11 on its axis to a position as shown in FIG. 7. At the same time, the arms 30 are positioned to limit movement of the billet 11. Then the hydraulic cylinder 70 is operated to move the members 66 to positions as illustrated in FIG. 5 to lower the L-shaped members 64, the cylinder 68 being operable to allow each L-shaped member 64 to clear the billet and to then move each member 64 to the position of FIG. 4. Then the clamp arms 30 may be operated to clamp the billet in the position as illustrated in FIG. 3, positioning a new side of the billet for processing by the grinding mechanism.

After complete processing of the billet 11, the turning mechanism is used to again turn the billet and move it to a position in which it slides onto the run-in, run-out rollers 29. In this case, the arms 30 are positioned as depicted in FIG. 4. Then with the carriage in the position as shown in FIG. 3, the rollers 29 are driven to effect a run-out movement of the billet onto the receiving rollers 27. The details of drive of the rollers 29 are not illustrated but it will be understood that they are driven in synchronism from a common longitudinally extending shaft 74 coupled to the rollers 29 through suitable right angle gearing assemblies.

The shaft 74 is driven by an electric motor carried by the transversely movable frame structure 36. The frame structure 36 also carries a hydraulic system for operation of the cylinders 38, 68 and 70 including electrically controlled valves and a pump driven by an electric motor. Energizing and control signals are applied to the electric motors and valves of the movable carriage 12 through a cable 76 connected to a stationary cable feed-out and take-up mechanism 77.

The stationary end of cable 76 is connected through a cable 79 to a control unit 80 which is connected through a cable 81 to a probe portion of the grinding mechanism 13, through a cable 82 to a control portion of the grinding mechanism 13, and through a cable 84 to the optical sensing station 20 as diagrammatically illustrated. Cables 76 and 79 include conductors which transmit signals from transducers which are associated with the various moving parts on the carriage 12 to provide information as to the positions thereof and to obtain accurate control of movements thereof.

As is shown in FIG. 5, the grinding wheel 24 carries the eddy current probe 22 in a radially extending passage 23 thereof and during each revolution of the grinding wheel 24, the terminal end of the probe 22 moves into proximity to the surface of the billet and in a crack in the billet surfaces produces a pulse in the output of the probe 22.

The probe 22 is connected through a rotary coupling unit 86, such as a slip ring unit, and through the cable 81 to the control unit 80. As disclosed in the aforesaid prior application Ser. No. 407,656 filed on Aug. 12, 1982, the probe 22 may be mounted through a bristle arrangement in a manner such as to permit its terminal end to be maintained in flush alignment with the peripheral surface of the grinding wheel 24 while permitting wear of the grinding wheel 24. The probe is held against outward movement but is movable radially inwardly during wear of the wheel 24. A preferred type of eddy current probe as well as a probe circuit for use therewith are disclosed in the aforesaid prior application, the disclosure of which is incorporated herein by reference.

Figure 8:
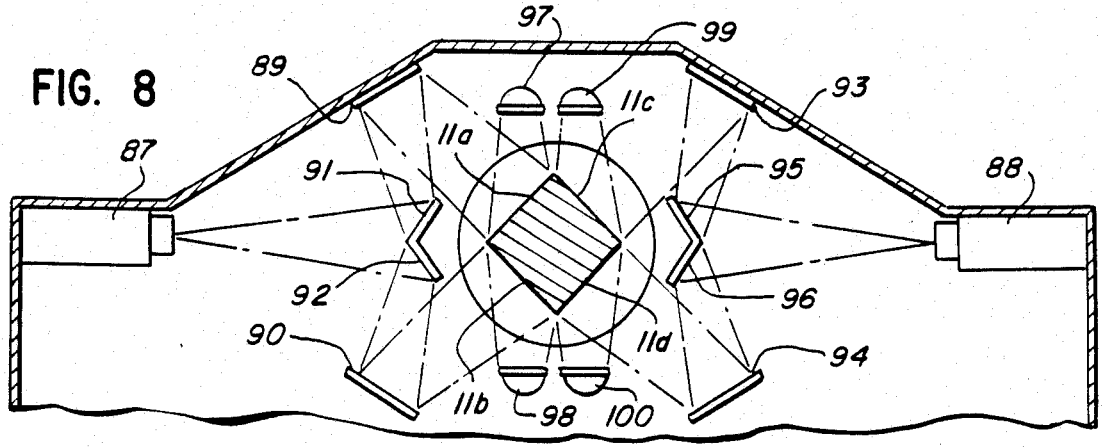
FIG. 8 is a sectional view taken substantially along line VIII—VIII of FIG. 1, diagrammatically illustrating an arrangement for detecting marks on a billet and recording the position thereof.

FIG. 8 diagrammatically illustrates an arrangement for detecting and recording the position of marks applies to the billet 11 during a prior inspection by means of apparatus such as the magnetic particle inspection apparatus 16. In the illustrated arrangement, two television cameras 87 and 88 are provided, each being arranged to obtain an image of two surfaces of the billet 11. Camera 87 produces an image from surfaces 11a and 11b of the billet 11, projected to the camera 87 by means of a first pair of mirrors 89 and 90 and a second pair of mirrors 91 and 92. Similarly, camera 88 develops an image from surfaces 11c and 11d of the billet 11, projected to the camera 88 using a third pair of mirrors 93 and 94 and a fourth pair of mirrors 95 and 96. Lights 97, 98, 99 and 100 are provided for illuminating the surfaces 11a, 11b, 11c and 11d of the billet. Preferably, the lights 97-100 are ultraviolet lights for detection of marks containing a fluorescent material.

It will be understood that other types of systems may be used for detecting marks on the four surfaces of the billet. Four television cameras may be provided, or a single camera may be used with rotation relative to the billet or with a suitable mirror arrangement, to obtain images from all four surfaces of the billet. Detection means other than television cameras may be used.

Figure 9:
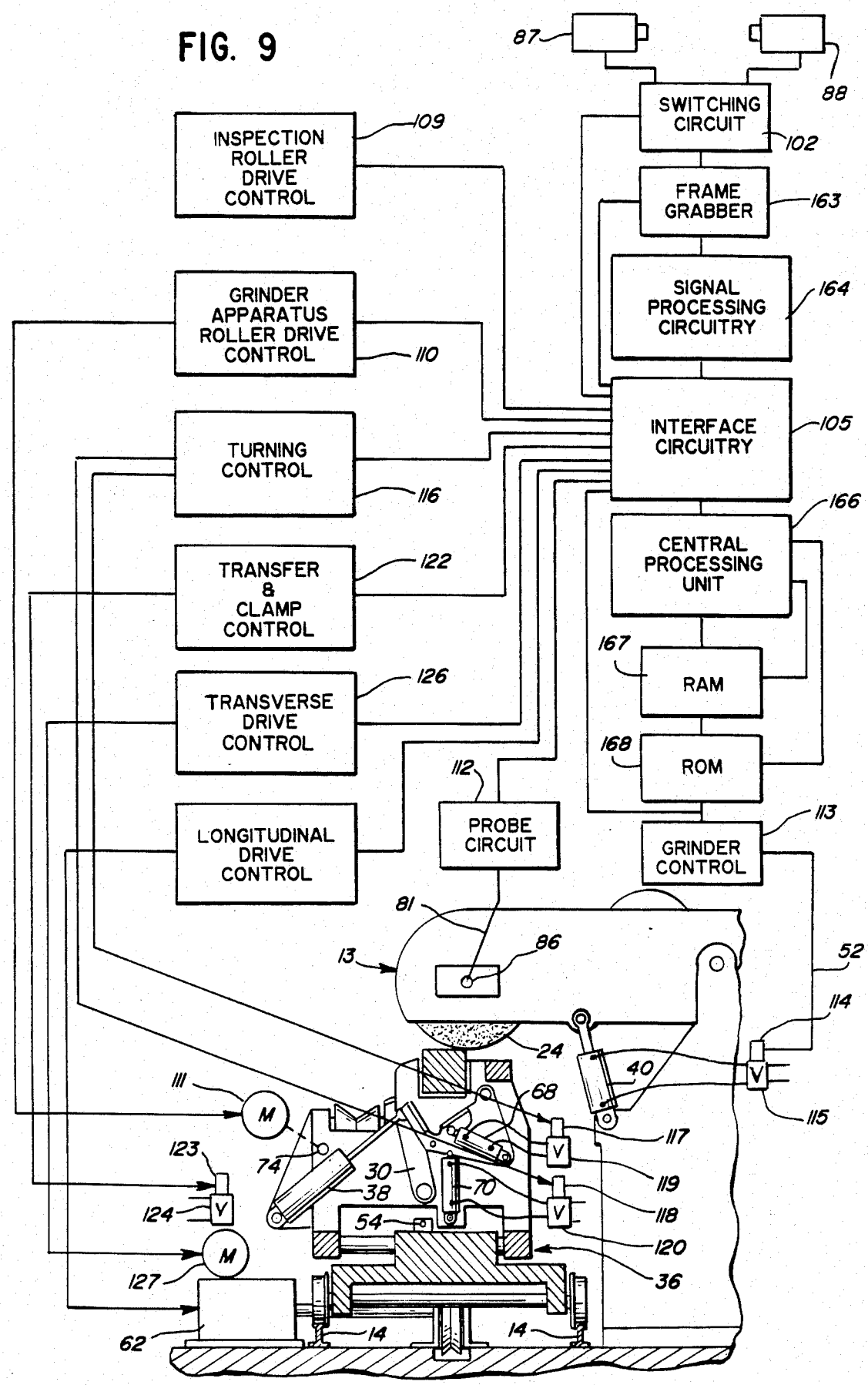
FIG. 9 is a schematic block diagram showing electrical control circuits of the system, also diagrammatically showing the connection of the electrical control circuits to operating components of the system.

As shown in FIG. 9, the cameras 87 and 88 are connected through a switching circuit 102 to a frame grabber circuit 103 which is connected to signal processing circuit 104, circuits 102, 103 and 104 being connected through interface circuitry 105 to a central processor unit 106. The processor unit 106 is connected to a random access memory 107 as well as a read only memory 108. The processor unit 106 is also connected through the interface circuitry 105 to a roller drive control 109 of the inspection apparatus as well as to a roller drive control 110 of the grinding apparatus. Roller drive control 110 of the grinder is connected to a drive motor 111 for the shaft 74 from which the drive rollers 29 are driven and roller drive control 109 is connected to a similar drive motor of the inspection apparatus 16.

In operation, the roller drive controls 109 and 110 are operated in synchronism for moving the billet 11 from the inspection apparatus 16 to the grinding apparatus. During such movement, the television cameras 87 and 88 are operated and at predetermined positions of the billet, frames of video signals are converted into digital form by the signal processing circuitry and are recorded in the random access memory 107. When the billet 11 reaches the position shown in FIG. 1, the memory 107 contains a record of the position of all marks on all four faces of the billet 11.

The central processor unit 106 is also connected through the interface circuitry 105 to control circuits which control billet handling and grinding operations and to a probe circuit 112 which is connected through the cable 81 and through the rotary coupling unit 86 to the probe 22.

A grinder control circuit 113 is connected through conductors of the cable 82 to a solenoid unit 114 which operates a valve 115, for control of flow of hydraulic fluid to the cylinder 40 which controls the vertical position of the grinding wheel 24. It will be understood that a conventional hydraulic system is provided including a pump driven by an electric motor and a reservoir.

A turning control circuit 116 is connected to solenoid units 117 and 118 which control valves 119 and 120 for control of flow of hydraulic fluid to and from the cylinders 68 and 70.

Also, a transfer and clamp control circuit 122 is connected to a solenoid unit 123 to control a valve 124 which controls supply fluid to and from the cylinder 38.

A transverse drive control circuit 126 is connected to a motor 127 for driving the shaft 54. As has been indicated, lead-screw assemblies are driven from the shaft 54 for effecting transverse movement of the movable carriage 36.

It is noted that the hydraulic system for supplying hydraulic fluid for operation of the cylinders 38, 68 and 70 and the motors 111 and 127 are all supported on the carriage 12, either on the transversely movable section 36 or on the base section 48 and that electrical power for operation thereof is supplied through the cable 76.

To control longitudinal movement of the carriage 12, the motor 62 is connected to a longitudinal drive control circuit 128. The control circuits 91, 94, 100, 104, 106 and 108 are all connected through the interface circuitry 105 to the central processor unit 106.

Figure 10:
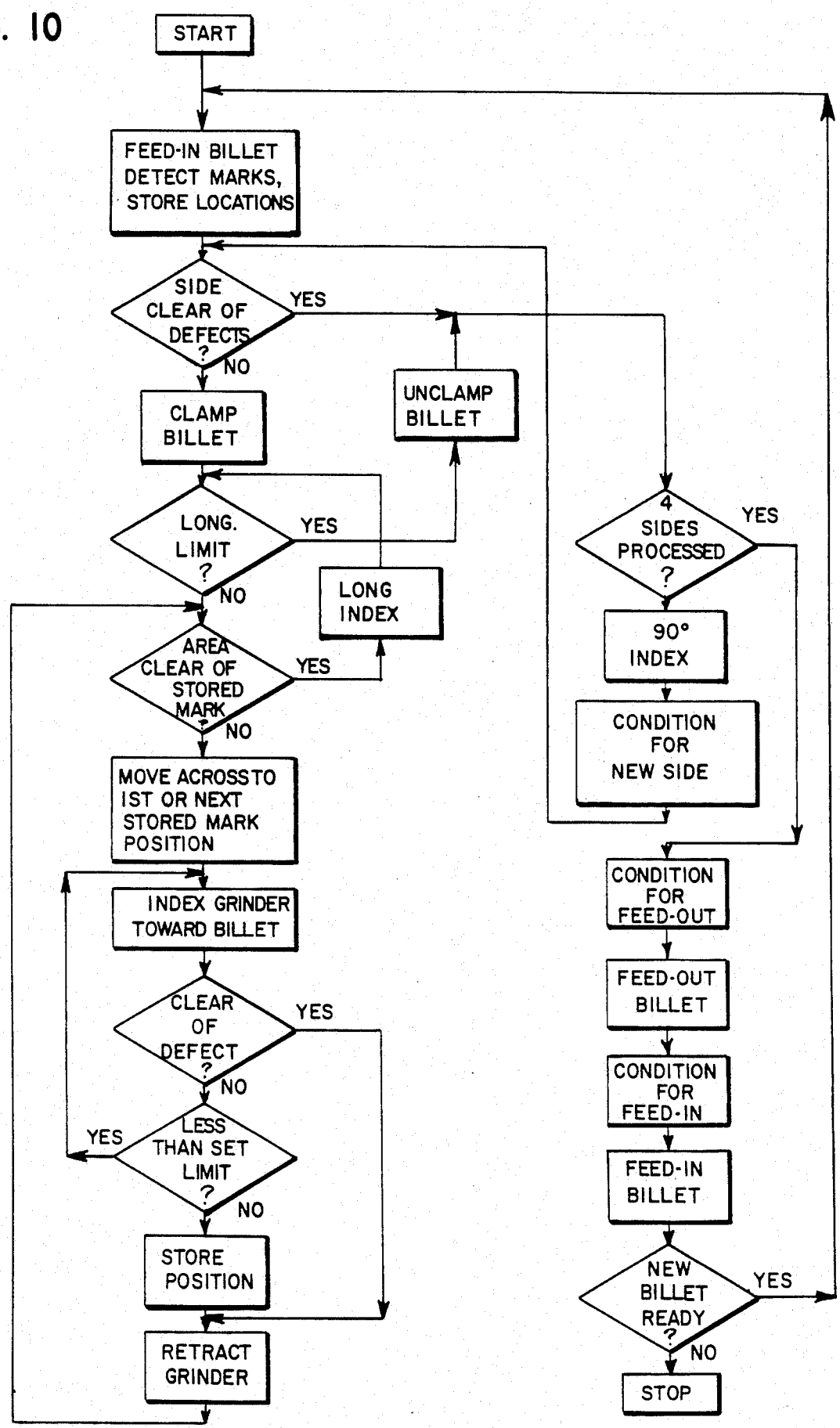
FIG. 10 is a flow chart showing the mode of operation obtained with one type of processing arrangement.

FIG. 10 is a flow chart illustrating the steps performed in inspection of the billet 11 in one mode of operation. First, the billet is fed in longitudinally from the inspection apparatus 16 and onto the carriage with marks being detected and the positions thereof being stored during the feed-in operations. With the camera arrangement of FIG. 8 and the circuit arrangement of FIG. 9, a feeding operation may be effected by performing a series of longitudinal index operations, each being effected by rotating the rollers 29 and run-out rollers of the apparatus 16 through a certain angle. After each indexing operation, the frame grabber 103 is operated with the switching circuit 102 in one condition and signals developed by camera 87 from a raster scan of areas of the faces 11a and 11b are stored in RAM 107. Then the frame grabber 103 is operated with the switching circuit 102 in a second condition and signals developed by camera 88 from a raster scan of areas of the faces 11a and 11d are stored in the RAM 107. After a number of such indexing operations, a complete record of all defect indications is stored in the RAM 107 and at the same time, the billet is fed into a position to be clamped to the carriage.

After positioning the billet, the grinding control operation is initiated. A test of the data stored in RAM 107 is performed to determine that the entire side is not clear of any stored mark signals. If the side is not clear of defects, the billet is moved transversely and clamped and then a test is run to determine that the carriage is not at a longitudinal limit position. Then a test of the data stored in RAM 107 is performed to determine whether the memory is clear of any stored mark signal corresponding to the area in transverse alignment with the grinding wheel. If the memory is clear, a longitudinal index operation is performed by moving the carriage 12 through a certain incremental distance, using the motor 62 to drive the pulley or drum. If the memory is not clear, the billet is moved transversely, if necessary, to the first or next stored mark position. This operation is performed through operation of the transverse drive circuit 126, operating the motor 127. After moving tranversely to a position opposite the stored mark, the grinding wheel is indexed toward the billet 11 through operation of the grinder index control circuit 113, which controls operation of the cylinder 40.

After indexing the grinder toward the billet, the output of the probe is checked, through operation of the probe circuit 112 to determine whether the portion being engaged by the grinding wheel is clear of a defect. If it is, the grinder is retracted. If not, a check is made to determine whether the depth of the grinding operation is less than a set limit and if so, the grinder is again indexed toward the billet. If the depth is not less than the set limit, the position is recorded in a memory and then the grinder is retracted. With this feature, there is protection against an operation in which the grinder might grind away an excessive amount of the billet, but a record is made to provide an alert that the billet may be defective.

After the grinder is retracted, the memory is again checked to determine whether the memory is clear of any additional stored mark at the longitudinal position of the grinder relative to the billet. If not, the carriage is again moved transversely to a position corresponding to the next stored mark position and the grinder-index operation is repeated. If the memory is clear, however, the longitudinal index operation is repeated.

When the billet has been moved to a longitudinal limit position and unclamped or when a test of memory has shown that the entire side is clean of defects, a check is made to determine that all four sides have not been processed and if not, a 90 degree index operation is performed through operation of the turning circuit 116 which controls operation of the cylinders 68 and 70, the clamp arm control circuit 122 being also brought into operation to control movement of the clamp arms 30.

After the 90 degree index operation, the apparatus is conditioned for processing of a new side, by conditioning the longitudinal index circuit to operate the motor 62 to index in the reverse direction, the processor 106 being conditioned to read in a corresponding direction from the flow indicating signals in the memory 107.

After conditioning for processing of a new side, grinding operation is again initiated in the manner as described above.

When all four sides have been processed, the apparatus is conditioned for a billet feed-out operation which is accomplished by moving the carriage to the position as illustrated in FIG. 3, if it is not already in that position, and by moving the billet 11 transversely back onto the position as illustrated in FIG. 3 in which it is supported on the rollers 19. This transverse movement is controlled through use of the turning circuit 116 in conjunction with the circuit 122 which controls operation of the arms 30.

Then the billet is fed out by driving the rollers 29 and simultaneously driving the rollers 27 of the receiving section 26.

Then the apparatus is conditioned for a billet feed-in operation, by moving the carriage back to the position as shown in FIG. 1. Then if there is a billet ready in the magnetic particle inspection equipment 16 and if the apparatus is otherwise ready to receive a new billet, the feed-in, mark detection and location storage operations are repeated. If not, operation of the system is stopped.

Figure 11:
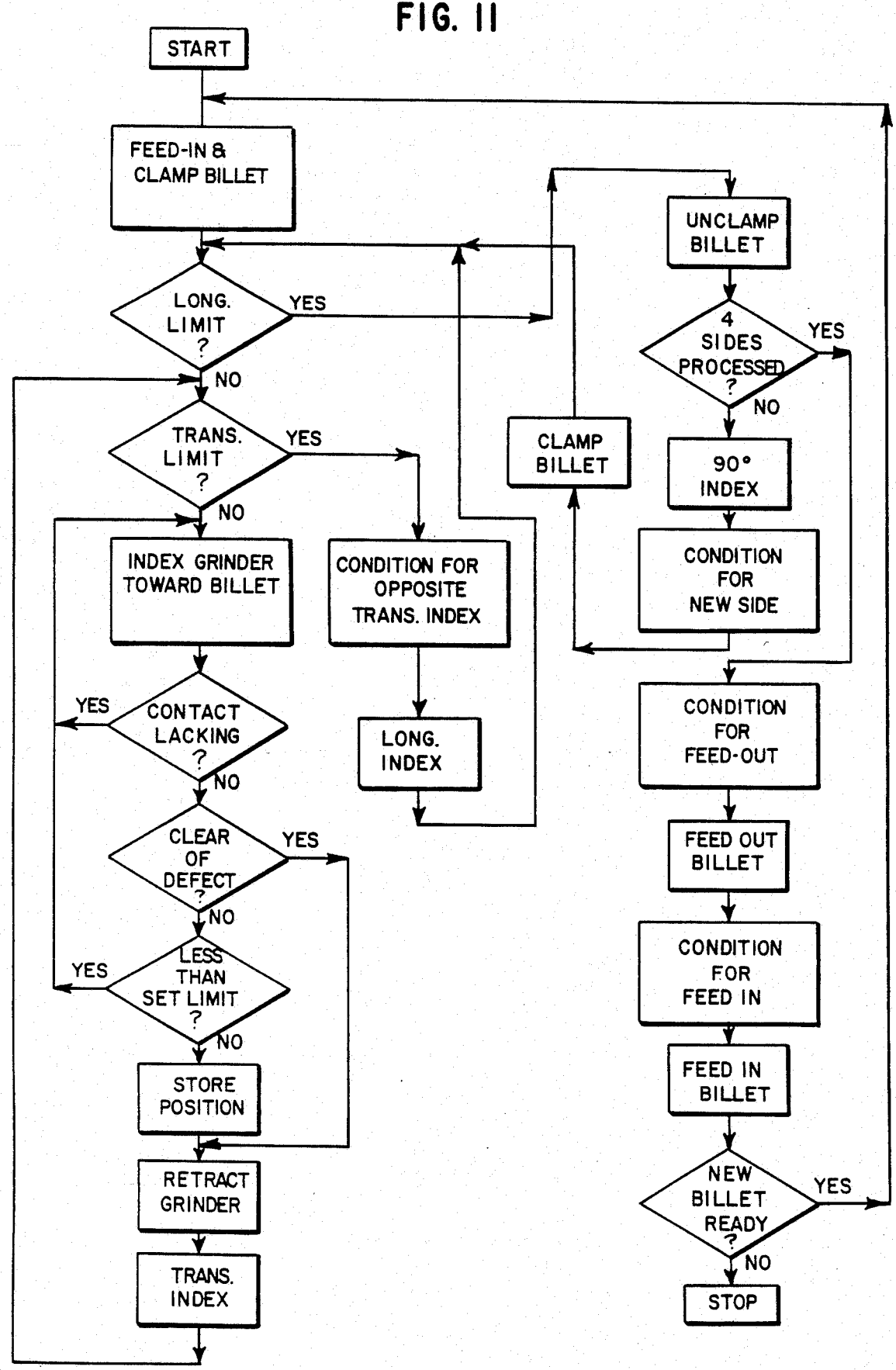
FIG. 11 is another flow chart showing another type of operation obtained with the system.

FIG. 11 is a flow chart illustrating the steps performed in inspection of the billet 11 in another mode of operation which does not involve prior inspection of the billet by magnetic particle inspection or otherwise and which does not require use of the detecting and recording arrangement of FIG. 8. The billet is fed in and clamped and then tests are performed to determine that the billet is not at longitudinal and transverse limit positions. If not, the grinder is indexed toward the billet, through use of the control circuit 91, controlling operation of the cylinder 40. A test is then made to determine whether the grinding wheel is engaging the billet, which is accomplished through monitoring of the signal developed by the probe circuit 87. If engagement is lacking, the grinder is again indexed toward the billet. Once the wheel engages the billet, the output of the probe circuit 87 is sampled to determine whether the billet is clear of a defect. If it is, another index operation is initiated. If not, and if the depth is less than the set limit, the grinder index operation is repeated. Once the set limit is reached, the position is recorded and the grinder is retracted.

Then a transverse index operation is performed and if a transverse limit has not been reached, the grinder is again indexed toward the billet, the grinding operation being repeated. When a transverse limit position is reached, the equipment is conditioned for indexing operations in an opposite transverse direction and a longitudinal index operation is performed, the longitudinal limit test being again performed.

When a longitudinal limit position is reached, the billet is unclamped and, if all four sides have not been processed, the billet is rotated 90° and the equipment is otherwise conditioned for processing of a new side, the billet being again moved to the clamped position.

When all four sides have been processed, feed-out and feed-in operations are performed in the same manner as indicated in the flow chart of FIG. 10.

With the mode of operation as depicted in the flow chart of FIG. 11, the grinder moves in a zig-zag path over the entire surface of each of the four sides of the billet, removing at least a thin layer therefrom to determine whether there is a defect. Thus, somewhat more material is removed than is the case with the operation of FIG. 10. However, the operation of FIG. 11 does not require the prior inspection through the magnetic particle method or otherwise.

Figure 12:
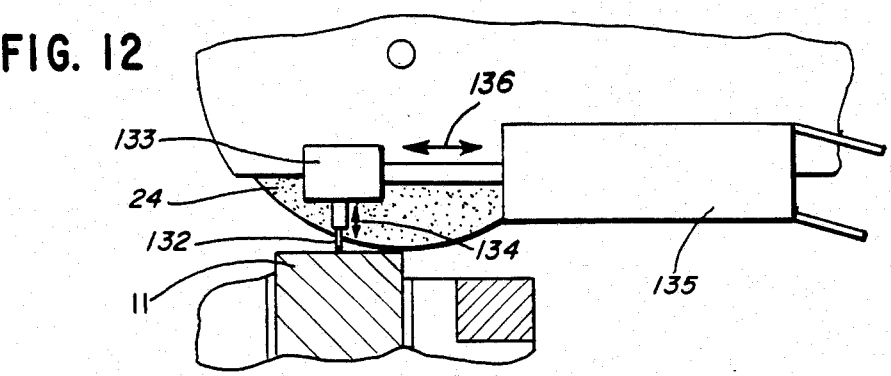
FIG. 12 is an elevational view, partly in section, illustrating a modified arrangement in which a crack detecting probe is supported alongside a grinding wheel.

FIG. 12 illustrates a modification in which a probe 132 is provided for engagement with the billet 11 at one side of the grinding wheel 24. The probe 112 is preferably an eddy current probe and is supported from a carrier 133 which includes a mechanism operable to move the probe vertically toward or away from the surface of the billet 11, as indicated by the arrow 134. The carrier 133 is supported from a stationary fixture 135 which includes a mechanism operable to cause horizontal movement of the carrier 133 in either direction, as indicated by the arrow 136, such movement being in a plane transverse to the longitudinal axis of the billet. The probe 132 is useable in perform the same function as the probe 22 in the grinding wheel 24 and with the probe 132, the probe 22 may be eliminated. However, with the probe 132, additional movements are required for detection of flaws and grinding since flaw detection is not accomplished simultaneously with the grinding operation.

Figure 13:
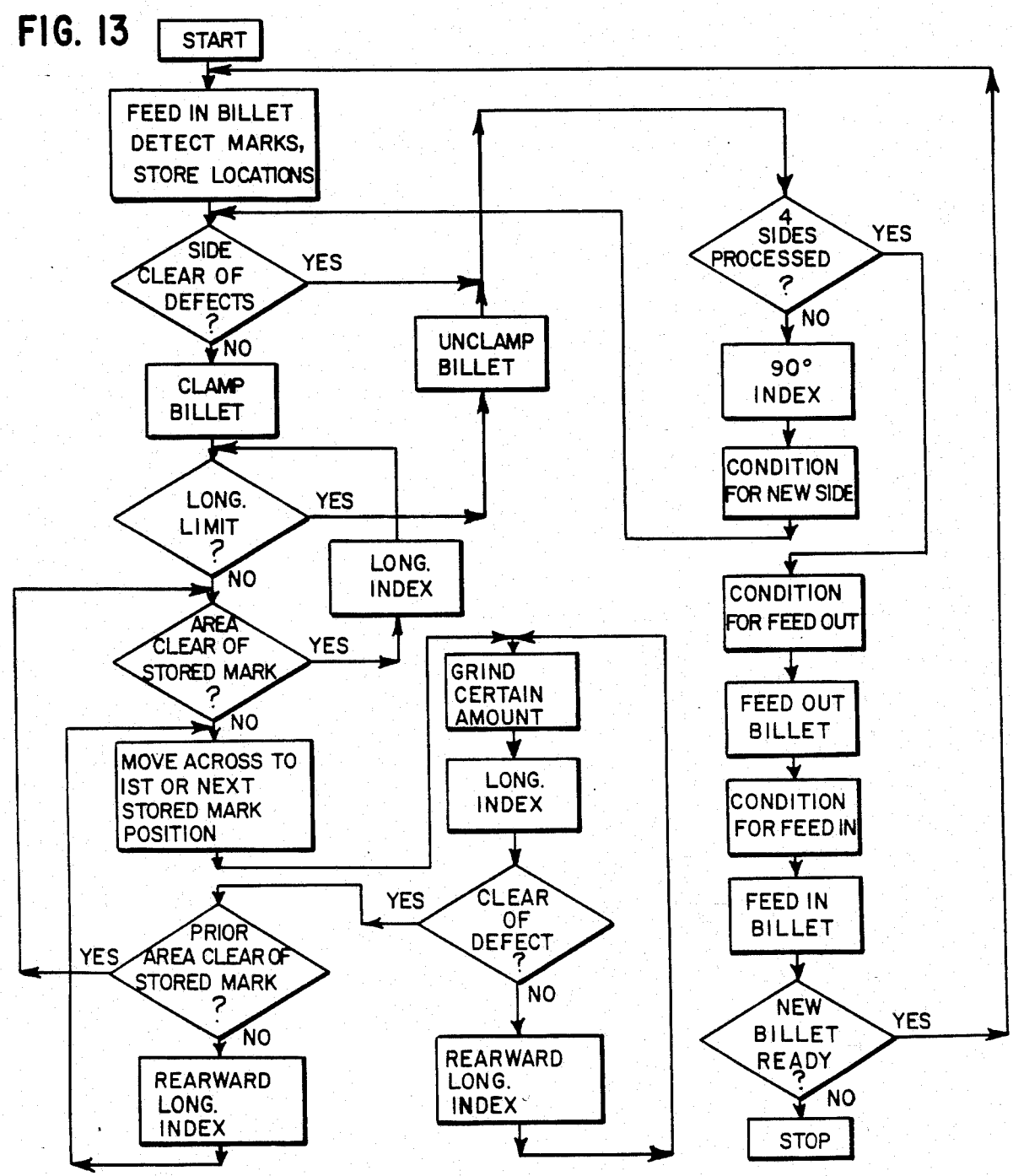
FIGS. 13, 14, 15 and 16 are flow charts showing operations with the modified arrangement of FIG. 11.

FIG. 13 is a flow chart illustrating the steps performed in inspection of the billet 11 in one mode of operation, using the separate probe 132 of FIG. 12. The initial steps are similar to those performed in the mode of operation illustrated in FIG. 10, the billet being fed in while detecting marks and storing the locations thereof and the billet being clamped if the entire side is not clear of stored mark locations. Then after testing to determine that the carriage is not at a longitudinal limit position, a test is made with respect to marks in the area in transverse alignment with the grinder. If there are no stored marks, the billet is moved transversely to the first or next stored mark position. Then the grinder is operated automatically to move toward the billet and to grind away a certain amount of material, grinding to certain depth. After doing so, the billet is indexed forwardly and a test is performed by moving the probe 132 into engagement with the surface portion of the billet on which the grinding operation has just been performed. If the signal from the probe 132 indicates that the portion tested has been cleared of a defect. If not, the billet is indexed longitudinally in the reverse or rearward direction to position the defective portion opposite the grinding wheel and another operation is performed in which a certain amount of material is ground away.

When the probe test indicates that the portion tested is clear of a defect, a test is made to determine whether the prior area, i.e., the area opposite the grinding wheel before the forward longitudinal index, is clear with respect to stored marks. If not, a rearward longitudinal index is performed and a transverse movement is effected to the next stored mark position. If the prior area is clear, the entire operation is repeated with respect to the new area.

The operation is continued until a longitudinal limit position is reached whereupon the billet is unclamped and turned as required until all four sides have been processed, in the same manner as described above in connection with the flow chart of FIG. 10.

Figure 14:
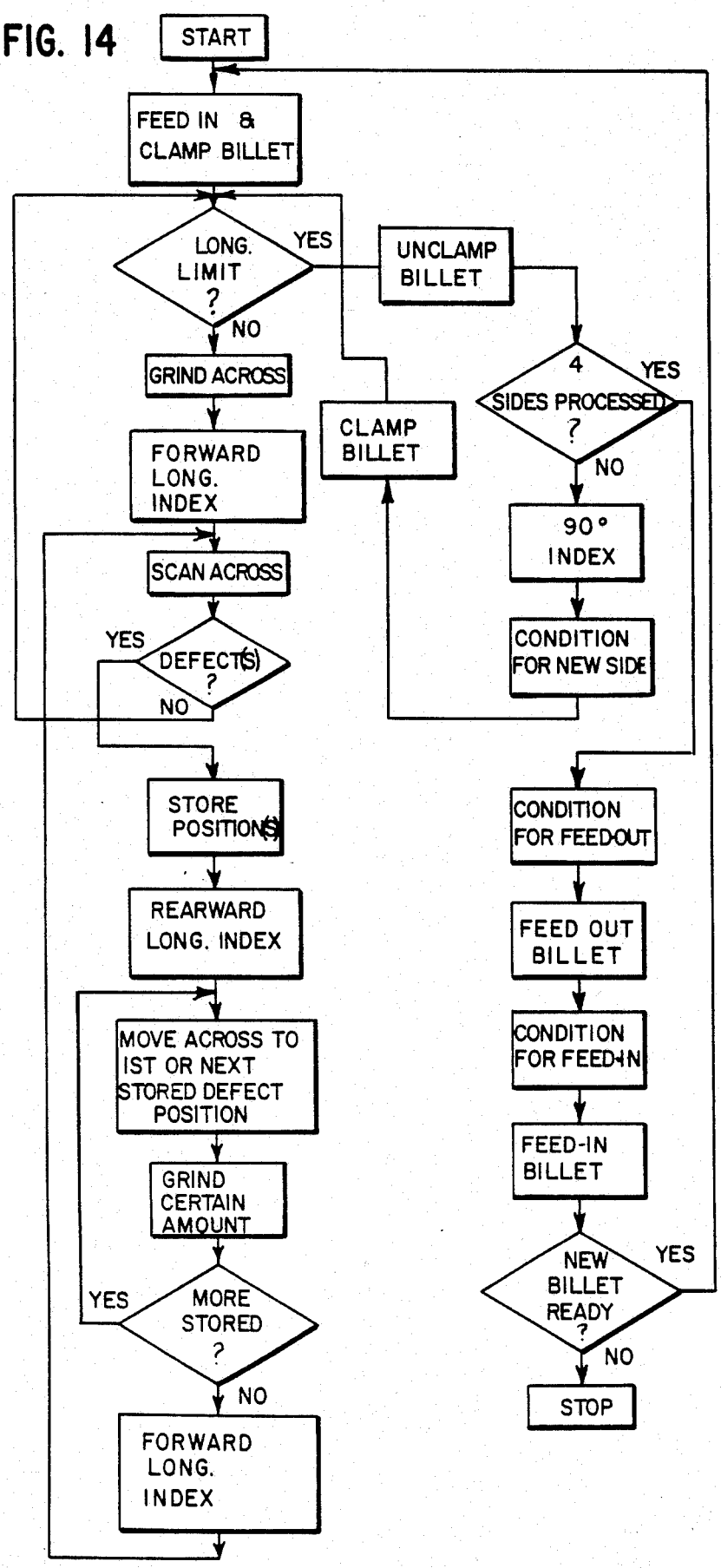

FIG. 14 is a flow chart illustrating the steps performed in inspection of the billet 11 in another mode of operation using the probe 132. This mode of operation does not involve prior inspection of the billet by magnetic particle inspection or otherwise and does not require use of the detecting and recording arrangement of FIG. 8. In the mode of operation as depicted in FIG. 14, the billet is fed in and clamped and then a grinding operation is performed in which, in effect, the grinding wheel is moved across the billet, removing a thin layer therefrom. Then the billet is indexed forwardly and a scanning operation is performed in which the probe 132 is moved across the billet, scanning the region from which the thin layer was removed. If one or more defect indications are obtained in the scanning operation, the positions thereof are stored and then the billet is indexed longitudinally in the reverse direction. Then the billet is indexed transversely to the first or next indicated defect and a grinding operation is performed in which a certain amount of material is removed. Then this operation is repeated until a certain amount of material is removed as to all defects detected in the scanning operation.

Then a forward index operation is performed and another scanning operation is initiated. This operation is repeated until all defect-containing material is removed at one longitudinal position.

When a longitudinal limit position is reached, the processing is continued as necessary until all four sides are processed, in the same manner as described above in connection with the flow chart of FIG. 10.

Figure 15:
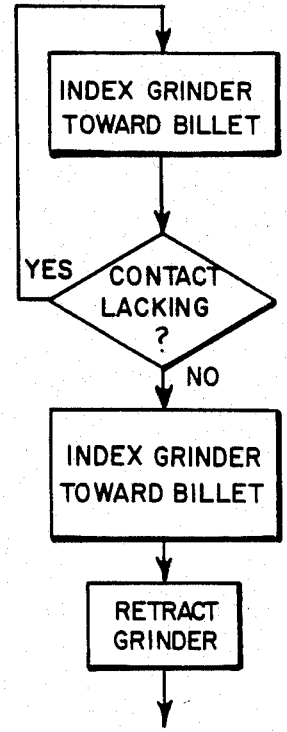

FIG. 15 is a flow chart illustrating the steps performed in grinding a certain amount of material from the billet, as performed in the operation depicted in FIG. 14, as well as in the operation depicted in FIG. 13. First, the grinder is indexed toward the billet, such indexing being repeated until engagement with the billet is detected, as by detecting an increase in load on the grinding wheel drive motor. Then another index operation is performed toward the billet to remove a certain amount of material therefrom and the grinding wheel is retracted.

Figure 16:
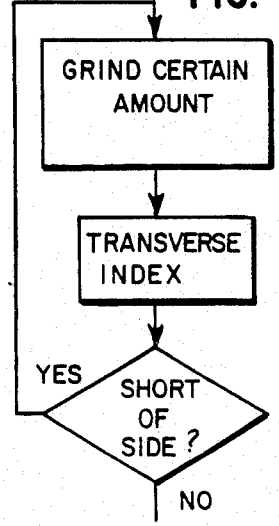

FIG. 16 is a flow chart illustrating the steps performed in the grind-across operation of FIG. 14. First, an operation is performed in grinding a certain amount of material from the billet, as illustrated in FIG. 14. Then a transverse index operation is performed and as long as the billet is short of a transverse end position, the operation is repeated. As a result, a layer of a certain thickness is ground away, across the surface of the billet.

Figure 17:
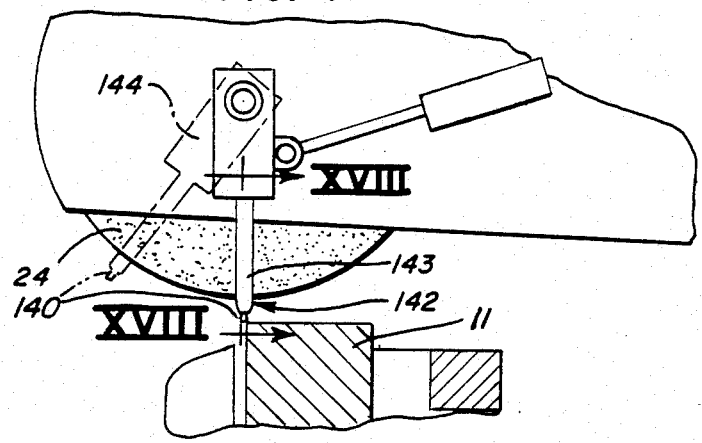
FIG. 17 is an elevational view similar to FIG. 12, illustrating another modified arrangement in which a crack detecting probe is supported adjacent a grinding wheel.
Figure 18:
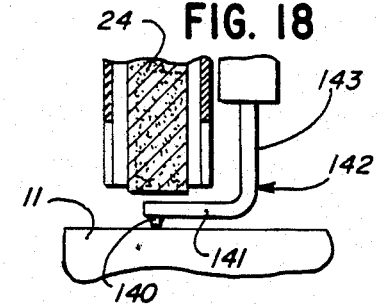
FIG. 18 is a sectional view taken substantially along line XVIII—XVIII of FIG. 17.

FIGS. 17 and 18 show a modification in which a probe 140 is carried at the end of one leg 141 of an L-shaped member 142 having a second leg 143 carried by an arm 144 which is journalled for pivotal movement about the axis of the grinding wheel 24. Preferably, a telescopic connection is provided between leg 143 and arm 144 with a spring operative to resiliently urge the probe 140 radially outwardly with respect to the axis of the grinding wheel 24 and to permit radially inward movement thereof when a force is applied overcoming the force of the spring. The probe 140 is thus resiliently engageable with the surface of the billet 11. The probe is electrically connected to conductors of a cable 145 through conductors extending through the member 142 and arm 144, member 142 and arm 144 being hollow for this purpose. To control pivotal movement of the arm 144, it is connected through a link 147 to a linear actuator 148.

With the grinding wheel 24 elevated to a position away from the billet, as shown, the actuator 148 is operable to move the arm 144 and thereby the probe 140 between positions as illustrated in dotted lines and positions as illustrated in full lines in FIG. 17. In the full line position, the probe 140 is engageable with a portion of the billet 11 directly under the grinding wheel 24 and by effecting transverse movement of the billet relative to the probe, the portion of the billet which is aligned with the grinding wheel 24 is scanned for detection of defects therein. Probe 140 may preferably be an eddy current probe but other types of probes may be used.

Figure 19:
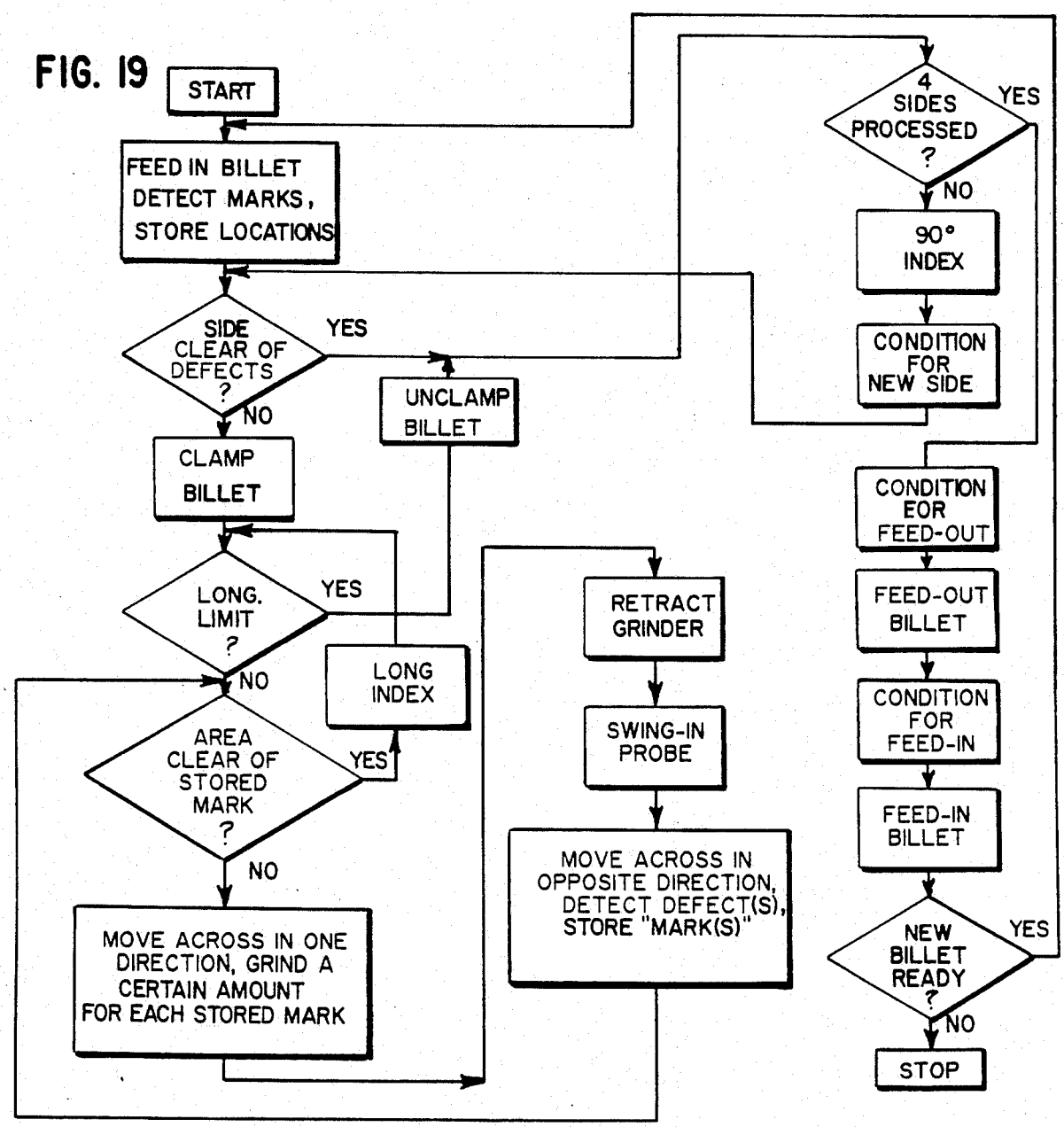
FIG. 19 is a flow chart illustrating one mode of operation with the modified arrangement of FIGS. 17 and 18.

FIG. 19 is a flow chart illustrating steps performed in one mode of inspection using the arrangement of FIGS. 17 and 18. The operation is similar to that shown in FIG. 10 but differs therefrom in that when a test of the data stored in RAM 107 indicates that the memory is not clear of stored mark signals corresponding to the area in transvere alignment with the grinding wheel, the billet is moved transversely in a forward grinding direction while the grinding wheel is moved into engagement therewith to grind a certain amount for each stored mark. Then the grinding wheel is retracted upwardly and the actuator 148 is operated to move the probe 140 inwardly to the position shown in full lines in FIG. 17. Then the billet is moved transversely in a reverse direction while using the probe 140 to detect defects, the positions of any detected defects being stored in RAM 107. Then if a test of the data stored in RAM 107 indicates that defects were detected, the billet is again moved in a forward grinding direction, the operation being continued until all defects are removed.

Figure 20:
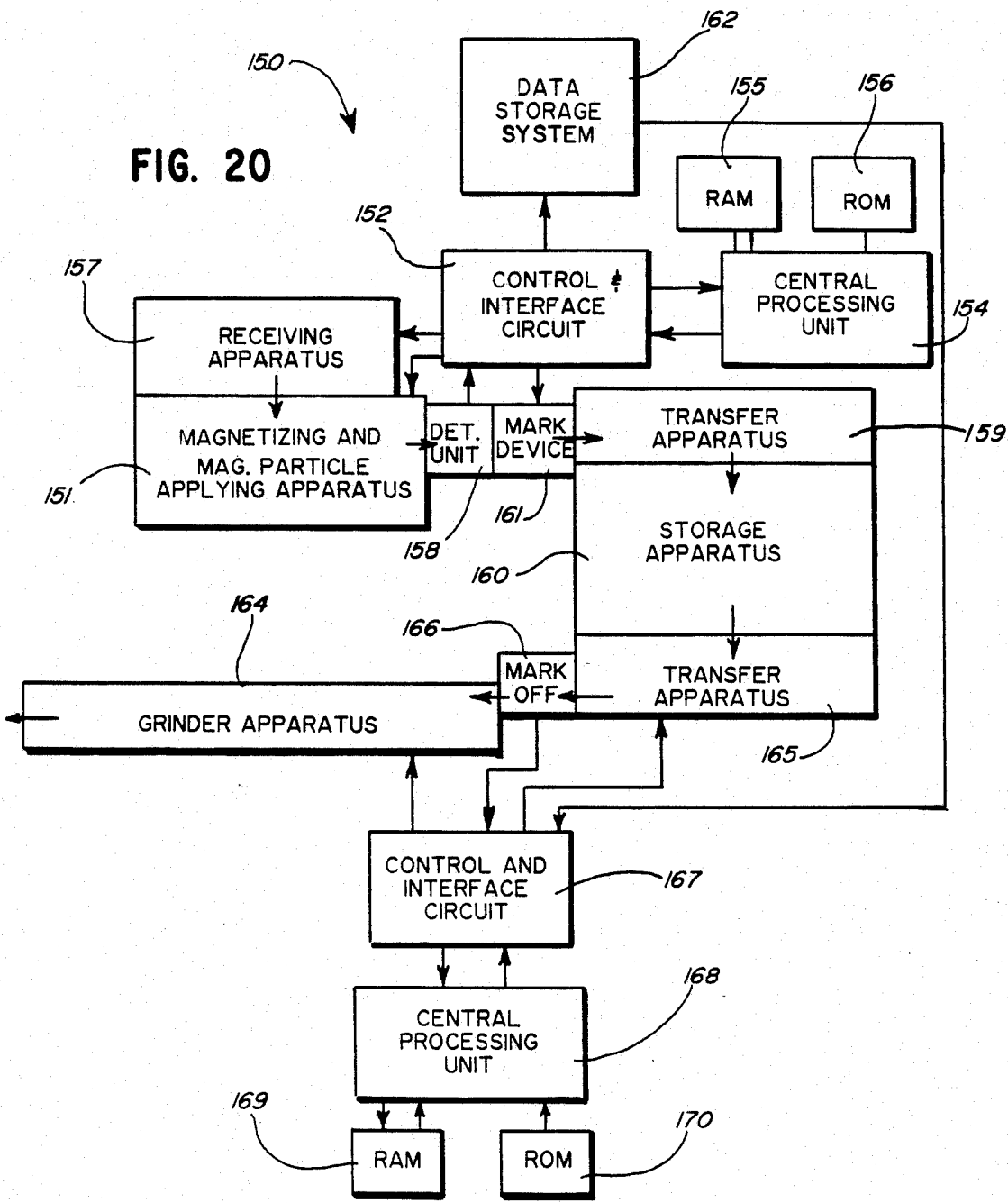
FIG. 20 is a schematic block diagram of a modified system.

FIG. 20 illustrates a modified system 150 in which an initial inspection of a billet is performed automatically while data is stored, the billet being marked for identification and then placed in storage for a subsequent grinding operation which is performed automatically after detection of the indentification mark and recall of the stored data.

In the system 150 as diagrammatically illustrated, magnetizing and magnetic particle applying apparatus 151 is connected through a control and interface circuit 152 to a central processor unit 154 which is connected to a random access memory 155 and a read only memory 156. Billets are transferred to the apparatus 151 from receiving apparatus 157. After magnetization and application of magnetic particles thereto, the billets are moved through a detector unit 158 to transfer apparatus 159 which operates to transfer billets to storage apparatus 160. A marking device 161 is provided for applying a mark to each billet as it is inspected and a data storage system 162 is provided for storage of data developed by the detector unit 158. Device 161 and the data storage system 162, as well as the detector unit 158 and receiving apparatus 157 and transfer apparatus 159 are connected through the control and interface circuit 152 to the central processor unit 154.

In operation, a billet is magnetized and magnetic particles are applied thereto to be concentrated over cracks or other defects in or near the surface of the billet to thus provide indications of such defects. Such indications are detected by the detector unit 158 which may include a television camera arrangement similar to that illustrated in FIGS. 8 and 9. In the alternative, laser scan arrangements may be used such as illustrated in U.S. Pat. No. 3,774,030 of O'Conner et al.

The electrical signals developed by the detector unit 158 are converted to digital signals which are stored in the data storage system 162, under control of the central processor unit 154, in accordance with the location of the defect, information being stored which identifies each detected defect with respect to a particular identified face of the billet on which it is located, the longitudinal position of the defect along the identified face and the transverse position of the defect on the identified face. The marking device 161 applies an identification mark which identifies the particular billet and also the orientation of the faces thereof.

The inspected billets are transferred from the storage apparatus 160 to grinder apparatus 164 by transfer apparatus 165. In moving from the transfer apparatus 165 to the grinder apparatus 164, the billets move through a mark detector 166 operative to detect the marks placed on the billet by the mark device 161. The grinder apparatus 164, transfer apparatus 165 and mark detector 166 are connected through a control and interface circuit 167 to a central processor unit 168 which is connected to a random access memory 169 and a read only memory 170. The data storage system 162 is also connected through the control and interface circuit 167 to the central processor unit 168.

The grinder apparatus 164 may preferably be constructed as illustrated in FIGS. 1-9, differing therefrom in that the optical sensing station 20 may be used only for detecting identification marks and it may, of course, be of simplified form. It is also possible, of course, to use the modified probe arrangement of FIG. 12 or the modified probe arrangement of FIGS. 17 and 18. In either case, the grinder apparatus is controlled from data stored by the data storage system 162 to effect the removal of defective portions of the billet.

With the system of FIG. 20, the identification marks should be reasonably permanent, but it is not necessary that permanent defect-indicating marks be applied by the apparatus 151 and the billets may be transported long distances or stored for indefinite periods of time after being automatically inspected and before being transferred by apparatus 165 to the grinder apparatus 164. In the data storage system 162, the digital data may be stored on disks or other media for retrieval when the grinding operation is to be performed. Thus, the portion of the system 162 controlled by the central processor unit 154 may be physically separate from the portion controlled by the central processor unit 168.

It is noted that other types of initial billet inspection may be used, in addition to or in place of magnetic particle inspection, including, for example, penetrant inspection, ultrasonic inspection, x-ray inspection and/or eddy current or leakage field magnetic inspection.

It is also noted that in the modes of operation as described and as depicted in the flow charts, a complete processing of one face takes place during one longitudinal pass in one direction, consisting of a series of longitudinal indexing movements with transverse movements or indexing operations occurring at times between longitudinal indexing operation. It is also possible to reverse the longitudinal and transverse operations to obtain a complete processing of one face during one transverse pass in one direction, consisting of a series of transverse indexing movements, with longitudinal movements or indexing operations occurring at times between transverse indexing operations. Thus, unless otherwise limited, the terms "transverse" and "longitudinal" should be construed as interchangeable. It is further noted that, in any case, indexing movements may be of small magnitude and performed in rapid sequence to obtain essentially continuous movements.

It will be understood that modifications and variations may be effected without departing from the spirit and scope of the novel concepts of the invention.

We claim:

1. Apparatus for processing rough-surfaced steel billets or like workpieces to remove cracked or otherwise defective portions thereof, comprising: workpiece support means, material removal means for coacting with a portion of a workpiece supported by said support means to remove material therefrom, positioning means for effecting relative movement of said workpiece support means and said material removal means, control means for controlling said positioning means, signal means including probe means associated with said material removal means and operative during coaction of said material removal means with a portion of the workpiece to detect defects in said portion and to apply corresponding defect signals to said control means, said positioning means being controlled through said control means to move in a predetermined scan pattern over a surface portion of the workpiece and to remove a thin layer of rough surface material therefrom and facilitate coaction of said probe means with said workpiece to develop a defect signal from any defective portion thereof, said positioning means being controlled through said control means for operation in the absence of a defect signal from said signal means to limit the depth of material removed and remove only said thin layer of rough surface material, and said positioning means being controlled through said control means and from a defect signal developed at any point during movement in said predetermined scan pattern to interrupt movement in said pattern, to then initiate removal of a defective portion at said point and to then continue removal of said defective portion at said point until removed and to thereafter continue movement in said scan pattern, whereby to effect removal of a thin surface layer and detection and removal of all defective portions in a single complete movement in said predetermined scan pattern.

2. In apparatus as defined in claim 1, said material removal means comprising a material removal element for engagement with the workpiece, and means for rotating said element about a certain axis, said probe means being supported for rotation with said element about said axis.

3. In apparatus as defined in claim 2, said material removal element being a grinding wheel and said probe means including a probe in the periphery of said grinding wheel.

4. Apparatus for processing workpieces in the form of elongated steel billets or the like to remove cracked or otherwise defective portions thereof, workpiece support means comprising a carriage and means for securely clamping a billet on said carriage, material removal means comprising a material removal element and means for rotating said element about a certain axis, positioning means comprising means for effecting movement of said element relative to said carriage in a first direction parallel to the longitudinal axis of said billet and in a second direction toward and away from said axis in a plane transverse thereto, said positioning means further comprising means for effecting movement of said element relative to said carriage in a third direction in a plane transverse to said longitudinal axis of said billet for relative movement of said element transversely across one face of said billet, control means for controlling said positioning means, signal means including probe means associated with said material removal means and operative during coaction of said material removal means with a portion of the billet to detect defects in said portion and to apply corresponding defect signals to said control means, said positioning means being controlled through said control means to effect movement in said first direction to index said element from one longitudinal position to another along the length of the billet and to effect at each longitudinal position a relative transverse movement in said third direction across one side of the billet, said element being moved over the entire surface area of one side of the billet during a single series of longitudinal indexing movements along the length of the billet, said positioning means being controlled through said control means during each transverse movement and in response to defect signals developed from said probe means to control movement of said element in said second direction to remove defective portions of the workpiece, whereby to detect and control removal of all defective portions on one side of the billet during said one series of longitudinal indexing movement along the length of the billet, and said probe means being supported for rotation with said rotating element to detect defects during coaction of said rotating element and the billet.

5. In apparatus as defined in claim 4, said positioning means being controllable by said control means upon completion of series of longitudinal indexing movements to initiate another series of longitudinal indexing movements in an opposite longitudinal direction until completion of sequential treatment of the four faces of the billet for removal of defective portions thereof.

6. In apparatus as defined in claim 4, said element being a grinding wheel.

7. In apparatus as defined in claim 4, said certain axis being parallel to the longitudinal axis of said billet.

8. In apparatus as defined in claim 4, inspection means for inspection of billets prior to operation of said material removal means to detect defects proximate the surface of said billet, said signal means including detection means for developing position signals in accordance with the positions of detected defects, and signal storage means controlled by said control means to store said position signals, said positioning means being controlled through said control means to position said material removal element along the billet in accordance with said position signals.

9. In apparatus as defined in claim 8, said inspection means comprising billet magnetizing and magnetic particle applying means operative to develop defect indications on the surface of said billet and said detector means comprising means for detecting said indications on the surfaces of said billet to develop said signals.

10. An apparatus as defined in claim 8, means controlled by said control means for effecting transfer of billets from said inspection means to said carriage with said detector means being operated by said control means during said transfer.

11. In apparatus as defined in claim 10, said positioning means being controlled from said control means to operate prior to each of said longitudinal indexing movements to respond to any stored position signal corresponding to the longitudinal position of said material removal means relative to the billet and to initiate removal of any corresponding defective portion with removal of any defective portion being continued at each longitudinal position in response to said defect signals developed from said probe means.

12. In apparatus as defined in claim 4, movement in said second direction being effected in a series of material-removal indexing movements, each movement performed after initial engagement with the billet being effective to grind a certain additional depth of material and being performed only in response to development of a defect signal following the preceding material-removal indexing movement.

13. In apparatus as defined in claim 12, means limiting the number of additional material-removal indexing operations performed after initial engagement of the billet.

* * * * *